United States Patent [19]

Lane

[11] Patent Number: 4,904,254

[45] Date of Patent: Feb. 27, 1990

[54] CORRECTION OF INCOMPETENT VENOUS VALVES

[75] Inventor: Rodney J. Lane, Cremorne, Australia

[73] Assignee: Vaso Products Australia PTY.Limited, North Sydney, Australia

[21] Appl. No.: 191,168

[22] PCT Filed: Jul. 13, 1987

[86] PCT No.: PCT/AU87/00215

§ 371 Date: Mar. 4, 1988

§ 102(e) Date: Mar. 4, 1988

[87] PCT Pub. No.: WO88/00454

PCT Pub. Date: Jan. 28, 1988

[30] Foreign Application Priority Data

Jul. 17, 1986 [AU] Australia .............................. PH6992
Feb. 10, 1987 [AU] Australia .............................. PI0270
Mar. 24, 1987 [AU] Australia .............................. PI1053

[51] Int. Cl.⁴ .......................... A61F 2/24; A61B 17/00
[52] U.S. Cl. .......................................... 623/2; 606/153
[58] Field of Search ................ 623/2; 128/346, 334 C

[56] References Cited

U.S. PATENT DOCUMENTS

| | | | |
|---|---|---|---|
| 2,756,753 | 9/1956 | Means | 128/325 |
| 3,254,651 | 6/1966 | Collito | 128/334 C |
| 3,357,432 | 12/1967 | Sparks | 128/334 C |
| 3,435,823 | 4/1969 | Edwards | 128/334 C |
| 3,726,279 | 4/1973 | Barefoot et al. | 128/327 |
| 4,602,911 | 7/1986 | Ahmadi | 623/2 |

Primary Examiner—Richard J. Apley
Assistant Examiner—Stephanie L. Iantorno
Attorney, Agent, or Firm—Lackenbach Siegel Marzullo & Aronson

[57] ABSTRACT

A cuff for restoring competence to an incompetent venous valve consists of a band of biocompatible implantable material that is not stretchable at blood flow pressures. The band is of sufficient length to encompass the vein at the site of the venous valve with the ends of the band overlapping. In one form of attachment, the end 22 passes over the loop 23 and is stapled thereto. The cuff can be attached to an applicator by means of the loop 23. A portion 26 of reduced thickness extends from the bottom face of the band to reduce any inner surface discontinuities with respect to the wall of the vein.

The cuff is placed around the vein at the site of the valve and the circumference of the cuff (and hence the diameter of the vein at the valve site) is reduced until competency of the valve in the vein is restored.

18 Claims, 8 Drawing Sheets

CORRECTION OF INCOMPETENT VENOUS VALVES

FIELD OF INVENTION

This invention relates to the correction of incompetent venous valves.

Venous valves in mammals are usually bicuspid valves, with each cusp forming a sack or reservoir for blood which, under pressure, forces the free edges of the cusps together to prevent retrograde flow of the blood and allow only antegrade flow to the heart. When an incompetent valve attempts to close in response to a pressure gradient across the valve, the cusps do not seal properly and retrograde flow of blood occurs.

There are two chronic venous diseases in which incompetence of venous valves is thought to be an important factor in the pathophysiology. These are varicose veins and chronic deep venous insufficiency.

The varicose vein condition consists of dilatation and tortuosity of the superficial veins of the lower limb and resulting cosmetic impairment, pain and ulceration. Primary varicose veins are the result of primary incompetence of the venous valves separating the superficial venous system from the deep venous system. Secondary varicose veins occur as the result of deep venous hypertension which has damaged the valves of the perforating veins.

Chronic deep venous insufficiency consists of deep hypertension of the lower limb with associated pigmentation, pain, swelling, ulceration and varicose veins.

For the sake of convenience, the invention will be described in relation to the correction of incompetent valves in the venous system of the lower limb in man, but, it is to be understood that the invention is not limited thereto.

The venous system of the lower limb consists essentially of the superficial venous system and the deep venous system. The superficial system includes the great saphenous vein and the small saphenous vein. The deep venous system includes the anterior and posterior tibial veins which unite to form the popliteal vein which in turn becomes the femoral vein when joined by the small saphenous vein.

The initial defect in primary varicose veins often involves localised imcompetence of a venous valve thus allowing reflux of blood from the deep venous system to the superficial venous system. This incompetence is traditionally thought to arise at the saphenofemoral junction but may also start at the perforators. Thus, gross saphenofemoral valvular dysfunction may be present in even mild varicose veins with competent distal veins. Even in the presence of incompetent perforators, occlusion of the saphenofemoral junction usually normalises venous pressure.

The initial defect in secondary varicose veins is often incompetence of a venous valve secondary to hypertension in the deep venous system. Since this increased pressure is manifested at many points, correction of one site of incompetence could clearly be insufficient as other sites of incompetence will be prone to develop. Apart from the initial defect, the pathophysiology is similar to that of varicose veins.

Once the initial incompetence occurs, incompetence in other valves in the system will tend to occur secondary to the venous hypertension.

Apparently, incompetence of venous valves is caused by dilatation of the vein wall. The evidence for this is as follows:

(i) The valves in varicose veins are normal macroscopically and histologically in most cases. The vein wall is more distensible in apparently normal veins in people with varicose veins.

(ii) The valve cusps have a much greater tensile strength than the vein wall.

(iii) Venous function deteriorates during the day as the venous system becomes more dilated.

(iv) Saphenofemoral valves which are incompetent can become competent again at operation when the diameter is decreased by spasm. A similar occurrence has been noted in the superficial femoral vein.

(v) Varicose veins may temporarily appear during pregnancy before the uterus is large enough to cause venous obstruction.

(vi) Forearm veins which are incompetent when full and distended can become competent again when the distal segment is emptied thus reducing the diameter. Valves which are competent can be made incompetent by injection of local anaesthetic which caused venodilatation.

Thus, it appears that dilatation of the vein wall, whether idiopathic (primary varicose veins) or secondary to venous hypertension (secondary varicose veins) leads to valvular incompetence. This dilatation may eventually lead to stretching and sclerosis of the valve. Other valves in the system will tend to become incompetent as the reflux of blood causes dilatation of the vein wall. We have found that it is possible to reverse or prevent the destructive process by overcoming this dilatation. Even if the vein wall weakness is generalised as appears to be the case with primary varicose veins, correction of the initial defect will delay or prevent stress being placed on that wall and thus hinder progression of the disease.

The fundamental change in flow in primary varicose veins is reflux of blood from the deep venous system into the superficial venous system, usually the great saphenous vein.

Traditionally, chronic deep venous insufficiency is regarded as being secondary to deep venous thrombosis which either obstructs the vein or is recanalised with associated destruction of the deep venous valves. The obstruction is initially prominent but as recanalisation occurs and collateral circulation develops, the obstruction is less prominent. Then the venous incompetence becomes more prominent. This syndrome follows deep venous thrombosis in a majority of cases.

Deep venous thrombosis is involved in the majority of cases of post-phlebetic syndrome but other factors such as site of deep venous thrombosis, obesity, muscle activity, posture and genetic predisposition may be involved. A primary incompetence of the venous valves appears to be involved in a significant number of cases.

BACKGROUND ART

In the main, prior art approaches to restoring competency of incompetent valves has involved venous reconstruction surgery of three basic kinds, namely, venous valve transplants, venous transposition and venous valvuloplasty.

As the term implies, the venous valve transplant approach involves the replacement of the segment of the vein having the incompetent valve with a segment of another vein having a competent valve. The venous transposition approach involves the redirection of the venous system so as to bypass an incompetent valve and venous valvuloplasty involves venous valve reconstructive surgery in which the free length of the valve cusps is reduced by plicating sutures.

These approaches to the prior art are well documented in A RATIONAL APPROACH TO SURGERY OF THE CHRONIC VENOUS STASIS SYNDROME by Harry Schanzer AND E Converse Peirce *ANNALS OF SURGERY* 1982, 195: 25–29 as well as in VALVULOPLASTY VALVE TRANSFER by Seshadri Raju Inter. Angio. 4 1985 419–424.

A single example on one patient of an experimental technique for treating an incompetent venous valve not involving the above types of venous surgery is described in an article by Dag Hallberg in *ACTA CHIR SCAND* 138: 143–145, 1972. Hallberg placed a band two to three millimetres larger than the diameter of the view around the vein.

The band was made of DACRON polyester and polyester and was applied when the patient was in the horizontal position. The band was retained loosely in position by several sutures in the venous adventitia.

Hallberg's method could not restore competence to the majority of the incompetent venous valves. In patients with venous disease, incompetent valves will usually be incompetent in the horizontal as well as the vertical positions. See, for example, FEMORAL VEIN RECONSTRUCTION IN THE MANAGEMENT OF CHRONIC VENOUS INSUFFICIENCY by Ferris E. B. and Kistner R., *ARCHIVES OF SURGERY*, 1982, 117:1571–1579.

Ferris and Kistner operated on 53 femoral veins in which the valves had been demonstrated pre-operatively to be incompetent. In only one case was the valve noted to be competent when the patient was horizontal at the time of operation. Kistner's approach was to suture the vein to prevent post-operative dilatation.

It is well known that by itself DACRON (Registered Trade Mark) polyester material causes marked fibrosis as well as foreign body reaction. Therefore, DACRON polyester cannot alone be considered biocompatible. In fact, DACRON polyester has been employed to stimulate fibrotic reactions which incorporate the synthetic fabric into tissue (see: S. Raju, ANN SURG. (1983) 197, 688–697).

The article REVASCULATION OF SEVERELY ISCHEMIC EXTREMITIES WITH AN ARTERIOVENOUS FISTULA by F. W. Blaisdell et al in AMERICAN JOURNAL OF SURGERY, Volume 112, pages 166–173 discloses problems associated with the use of DACRON polyester as an implantable material. In a number of cases, gradual narrowing of arteriovenous fistulas under a woven DACRON polyester sleeve was demonstrated.

In physical terms, the Hallberg approach was a static one. Once the cuff was sutured into position, no attempt was made to reduce the diameter of the vein at the valve site to restore competency of the valve. Indeed, Hallberg's single patient experiment was concerned with further dilatation of the vein at the valve site rather than reduction in the diameter of the dilated valve to restore competency.

DISCLOSURE OF THE INVENTION

It is an object of this invention to provide a method for restoring competence of incompetent venous valves by reducing the diameter of the appropriate vein at the valve site.

It is a further object of the invention to provide a method for restoring competence of incompetent venous valves in which the diameter of the vein at the valve site is adjusted to achieve proper competence of the valve and which permits clinical testing at the time of diameter reduction.

It is a yet another object of the invention to provide a device for restoring competence of an incompetent venous valve which is biocompatible and which does not require suturing to the vein itself.

According to one aspect of the invention there is provided a cuff for restoring competence to an incompetent venous valve, said cuff comprising a band of biocompatible implantable material that is not stretchable at blood flow pressures, the band being of sufficient length to encompass the vein at the site of the venous valve, with portions of the band overlapping, the overlapping portions being joinable together to form a cuff of desired circumference small enough to restore competence yet not too tight to decrease blood flow.

According to another aspect of the invention there is provided a method of restoring competency to incompetent venous valves comprising the steps of:

(i) placing a cuff of biocompatible material around the vein at the site of the valve, (ii) reducing the circumference of the cuff (and hence the diameter of the vein at the valve site) until competency of the valve in the vein is restored, and, (iii) fixing the circumference of the cuff at the point where the diameter of the vein is reduced to restore competency of the valve without impairing blood flow.

If necessary, the cuff is then secured to the surrounding tissue. Preferably, the circumference of the cuff around the vein is reduced in a stepwise fashion with the competency of the valve being tested between each stepped reduction in the circumference of the cuff. Competency of the valve may be tested by milking the vein, by the use of appropriate pressure detectors or by Doppler Techniques.

BRIEF DESCRIPTION OF THE DRAWINGS

In order that the invention may be more readily understood and put into practical effect, reference will now be made to the accompanying drawings in which.

DESCRIPTION OF PREFERRED EMBODIMENTS

Figure 1:
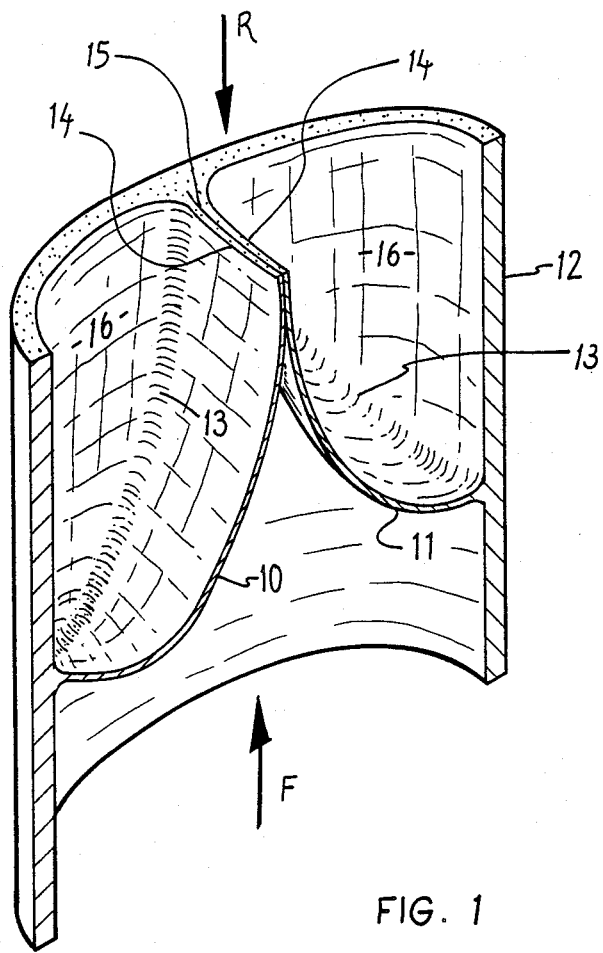
FIG. 1 is a cutaway diagrammatic perspective view of one side of a vein at a valve site with the valve in its closed disposition.
Figure 2:
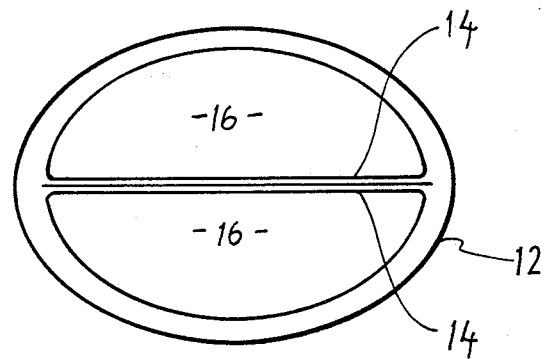
FIG. 2 is a plan view from above of the venous valve shown in FIG. 1.

The valves in the venous system of man are almost invariably bicuspid as is shown diagramatically in FIG. 1. Each cusp 10, 11 is semi-lunar and is attached to the wall of the vein 12 by its convex edge 13. The concave edges 14 lie free in the direction of normal blood flow indicated by arrow F. The attachment of each cusp approaches that of the other cusp proximally to form the commissure 15. Proximal to the valve, the vein is more distensible for about 1 cm. to form the sinus. In cross-section, when closed, the cusps 10, 11 of the valve meet in a straight line in the centre of the vein as shown in FIG. 2.

It will be appreciated that the venous valve is normally open with the free concave edges 14 separated by the upward flow of blood in the direction of arrow F. As will be apparent from FIG. 1, each cusp 10, 11 forms a sack or reservoir 16 for blood which, under pressure, in the direction of arrow R, forces the concave edges 14 together to prevent retrograde flow of blood-see FIGS. 1 and 3.

There are 10 to 20 valves in the great saphenous vein and 7 to 13 in the small saphenous vein. The perforating veins also have valves except for the feet where they are unusual.

On standing at rest, the pressure in both the superficial and deep venous system correlates closely with the hydrostatic pressure of a column of blood at the height of the atrium, about 80–90 mm. Flow in both superficial and deep systems is slow and is directed towards the heart (antegrade). Flow in the perforators is also slow but tends to be from the superficial venous system to the deep venous system. The flow in the foot is the reverse of that just described-from the deep veins in the sole of the foot to the superficial veins on the dorsum of the foot.

The position changes markedly on exercise. On calf contraction (systole) the pressure and flow in the deep system increases and flow through the perforators ceases. On calf relaxation (diastole) the pressure and flow in the deep system decrease and there is increased flow in the perforators from the superficial venous system to the deep venous system. The mean venous pressure drops during exercise by about 60–70 mmHg.

These changes are the result of the musculo-venous pump. As the muscle contracts, blood is expelled towards the heart. The blood is prevented from moving into the superficial system by the valves in the perforating system. On relaxation of the muscle the pressure drops but blood is prevented from reflux by the valves of the deep venous system and flow recommences from the superficial venous system to the deep venous system, through the perforators. The musculo-venous pump is responsible for efficient venous return in combination with the vis a tergo effect and of intra-thoracic and intra-abdominal pressure.

Figure 3:
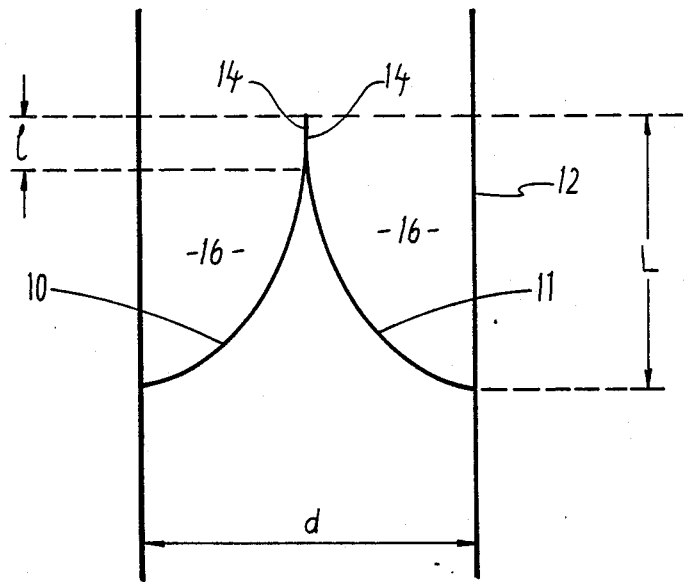
FIG. 3 is a schematic view of a competent venous valve in its closed disposition.
Figure 4:
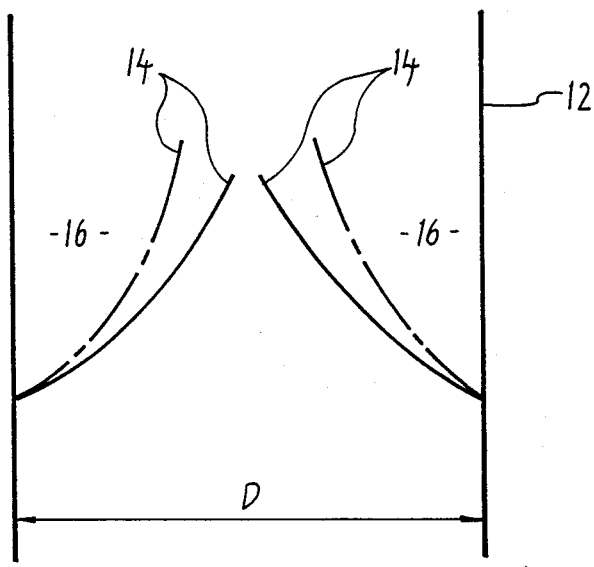
FIG. 4 is a schematic view similar to FIG. 3 but of an incompetent valve.

A competent valve is shown diagramatically in FIG. 3 in its closed disposition and an incompetent valve in FIG. 4. The cusps 10 and 11 of the competent valve in FIG. 3 form the blood sacks 16. The length of vein 12 at the valve site is indicated by "L" and the diameter of the vein, when the valve is competent, is indicated by "d". The extent of contact of the upper edges of the cusps when the valve is closed is indicated by "1".

When the diameter of the vein 12 is increased to "D" as shown in FIG. 4, the concave edges 14 of the cusps no longer meet and retrograde flow of blood can occur. The cusps 10a, 11a shown in dotted outline in FIG. 4 represent the normal disposition of the cusps and thus it can be seen that dilatation of the vein has led not only to separation of the cusps but also to a decrease in the general angle of the cusps to one another with a consequent lessening of the possible area of contact between the cusps should contact be possible at some diameter less than "D".

According to the present invention, it is possible to restore competence to an incompetent valve by decreasing the diameter of the vein wall at the valve site from the valve "D" of FIG. 4 towards but not necessarily to the diameter "d" of FIG. 3 by the use of a venous cuff.

Figure 5:
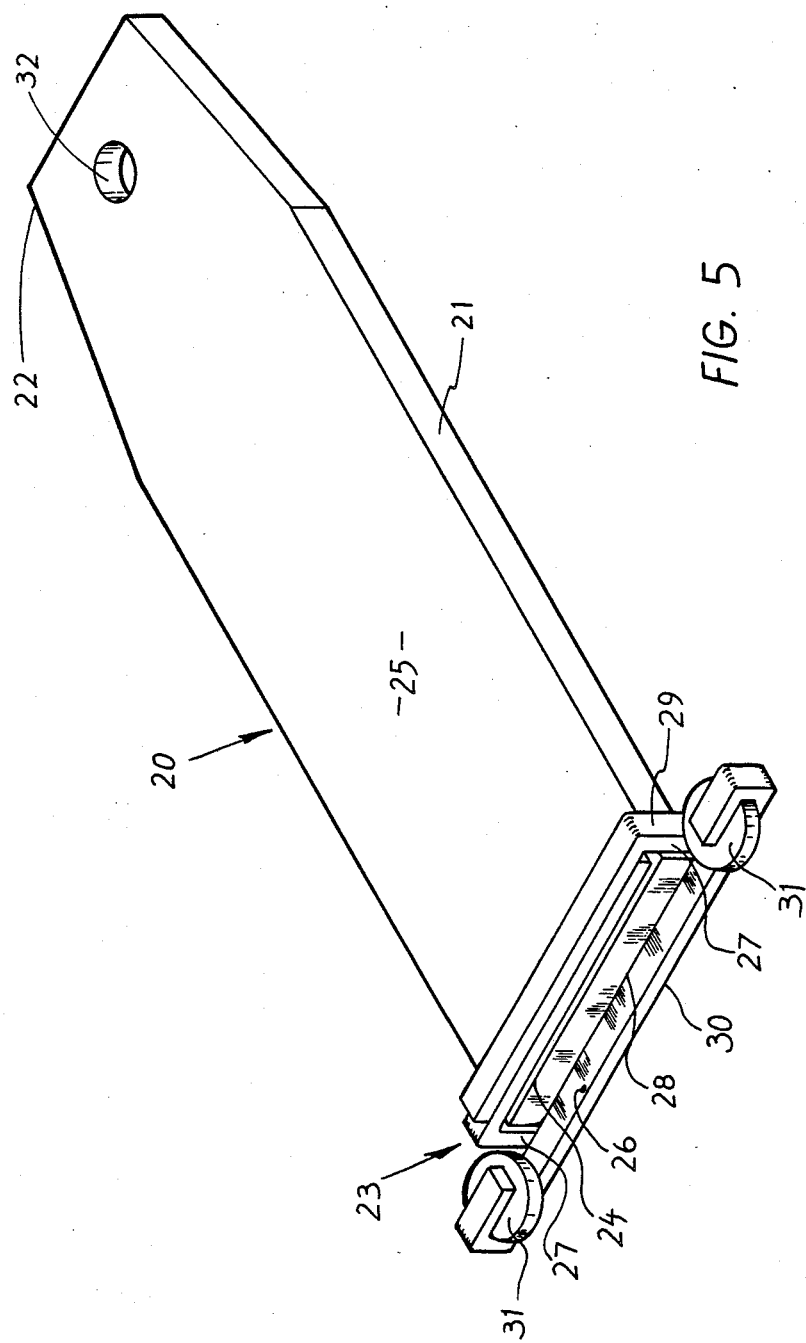
FIG. 5 is a perspective view of a venous cuff according to one embodiment of the invention.
Figure 6:
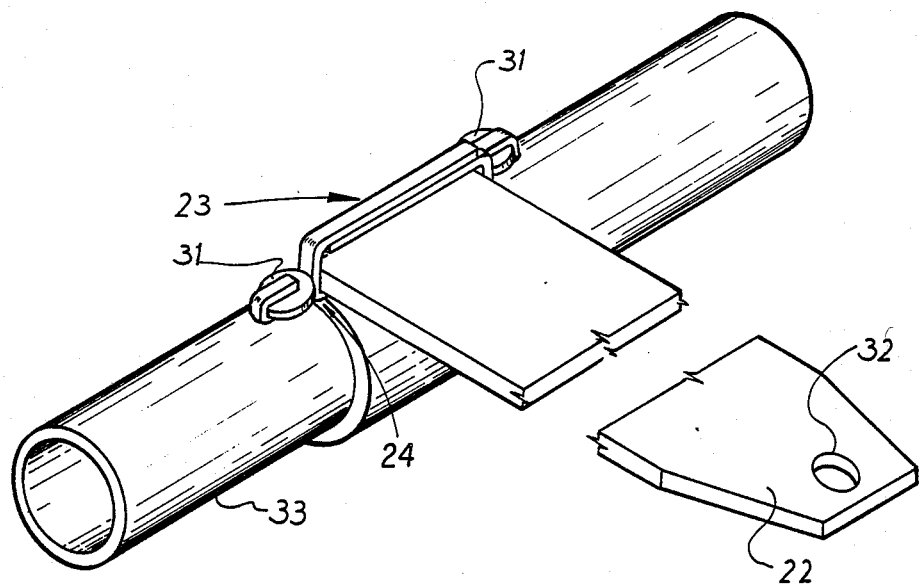
FIG. 6 is a perspective view of the cuff encircled around a vein.

The venous cuff 20 shown in FIGS. 5 and 6 is made of a bio-compatible material that does not significantly react with a vein or its surrounds and which in this instance, is flexible but does not stretch at the pressures encountered in blood flow. A preferred material is silicone rubber sheeting reinforced with embedded polyester fibres.

The venous cuff 20 consists of an elongated band 21 having a free end 22 and a loop 23 at its other end 24. As can be seen in FIG. 5, the loop 23 extends above the upper face 25 of the band 21 so that it may receive the free end 22 as shown in FIG. 6.

The loop 23 may be formed as a separate item that is glued to the band 21. In this instance, the loop 23 is formed from a flat rectangular strap 26 of polyester reinforced, Dow Corning Medical Grade silicone rubber sheet No. 501-1. The flat strap 26 has two straight slits 27 extending inwardly from the opposite edges of the strap and cut parallel to and 2 mm from the longitudinal side 28. The dimensions of the strap 26 according to one embodiment (which are given for illustrative purposes only) are as follows:

| Length | 48.0 (±0.5) mm |
| Breadth | 5.0 (±0.2) mm |
| Thickness | 0.178 (±0.076) mm |
| Slit length | 16.7 (+2–0.0) mm |

The slits 27 divide the loop 23 into an inner attachment portion 29 that is 2 mm wide and an outer deformable portion 30 that is 3 mm wide. The free ends of the attachment portion 29 are folded over one another to provide the loop 23. The free ends of the deformable portion 30 are each folded over themselves and secured between each folded portion by means of a suitable adhesive is a securing tab 31 by means of which the cuff may be sutured to neighbouring tissue.

In this instance, the band 21 is formed from a flat piece of polyester reinforced Dow Corning Medical Grade silicone rubber sheet No. 501-3. A hole 32 may be cut in the tapered end 22 of the band 21 for attaching the band 21 to a mechanical applicator. The dimensions of the band 21 according to one embodiment which are given for illustrative purposes only are as follows:

| Length | 68.0 (±0.5) mm |
| Breadth | 15.0 (±0.5) mm |
| Thickness | 0.503 (±0.076) mm |

| | |
|---|---|
| Taper Length | 20.0 (±0.5) mm |
| Taper Breadth | 10.0 (±0.5) mm |
| Hole diameter | 3.0 (±0.2) mm |

As will be apparent from the above dimensions, the deformable portion 30 is made from thinner material than the band 21 in order to decrease any possible effects that cuff surface discontinuities may have on the vein wall. The use of thinner material for the deformable portion 30 allows a smooth overlap inner surface on the cuff when implanted around a vein and allows the cuff to assume the shape of the vein.

As will be apparent from FIG. 6, with manual application of the cuff, the loop end 24 of the band 21 is placed on the vein 33. The band 21 is then encircled around the vein 33 and the free end 22 of the band 21 is passed through the loop 23. When the circumference of the cuff has been reduced to the point whereat the diameter of the vein is reduced to restore competency of the valve within the vein 33, the overlapping portions of the band 21 are fixed together by stapling or suturing and, if necessary, the free end 22 of the band 21 beyond the suture or staple is removed by any convenient means. The tabs 31 are then sutured to tissue surrounding the vein to prevent the cuff from sliding along the vein.

In an alternative method of application, the band could be looped in the other direction so that the free end of the band overlies the top of the loop.

Figure 8:
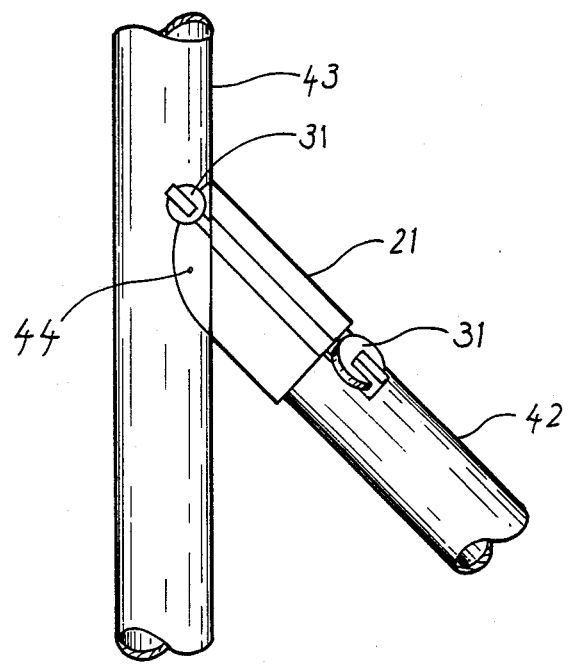
FIG. 8 is a side elevational view of the cuff shown in FIG. 7 in place at the junction of two veins.
Figure 9:
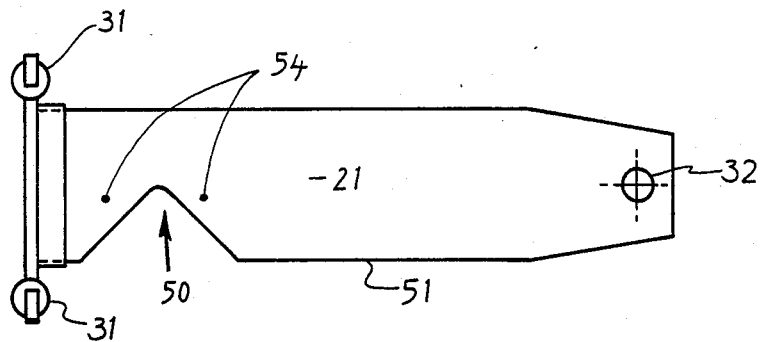
FIG. 9 is a plan view of a third embodiment of a venous cuff.

The modified form of the venous cuff shown in FIG. 8 is particularly suitable for restoring the competence of a valve in a first vein having a junction with a second vein of the kind shown in FIG. 9. The cuff is substantially similar to that shown in FIG. 5 and thus common elements share the same numerals.

A cut out portion 40 in the upper edge 41 of the band 21 is so dimensioned to enable the cuff to assume the shape shown in FIG. 8 when the cuff is positioned around a first vein 42 adjacent to its junction with a second vein 43.

The portions 44 of the band 21 adjacent to the cut-out 40 engage the vein as shown in FIG. 8 and the cuff is secured in position by means of one tab 31 being sutured to the tissue surrounding the vein 42 and the other tab 31 being sutured to tissue surrounding the vein 43.

Figure 7:
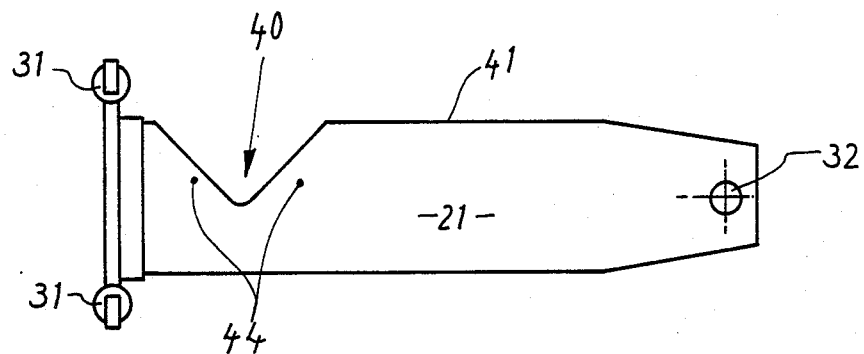
FIG. 7 is a plan view of a second embodiment of a venous cuff.

The cuff shown in FIG. 9 is substantially similar to that shown in FIG. 7 except that the cut-out 50 is in the lower edge 51 of the band 21. The cut-out 50 is so dimensioned to enable the cuff to assume the shape shown in FIG. 10 the cuff is positioned around a first vein 52 adjacent to its junction with a second vein 53.

Figure 10:
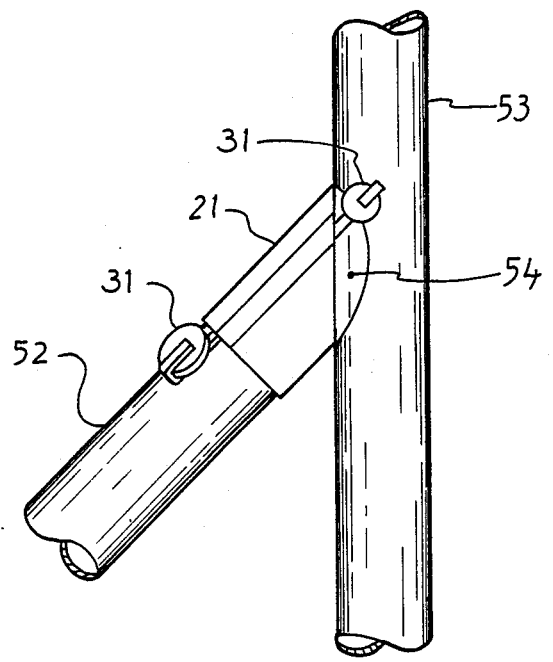
FIG. 10 is a side elevational view of the cuff shown in FIG. 9 in place at the junction of two veins.

The portions 54 of the band 21 adjacent to the cut-out 50 engage the vein 53 as shown in FIG. 10 and the cuff is secured into position by means of one tab 31 being sutured to tissue surrounding the vein 52 and the other tab 31 being sutured to tissue surrounding the vein 53.

It will be appreciated that the venous cuff may be made of any appropriate bio-compatible material that will not give rise to any significant adverse reactions within the body such as thrombosis, stenosis (i.e. narrowing of the vein) or perforation of the vein wall through wear and tear. The overlapping portions of the band 21 may be secured together in any convenient way-with or without the loop or buckle arrangement shown in the drawings. The overlapping portions may be secured together by stapling or suturing as described above, or by mechanical interlocking of parts of one portion with part of the other portion of the band at the overlap, or by adhesive, or by heat sensitive or pressure sensitive means.

If the overlapping portions of the band 21 are secured together by means external of the band such as by staples, sutures or adhesives, the external means should be selected so that there is no adverse interaction between the fastening means and the cuff or therein or surrounding tissue. It is preferred that neither the band nor the fastening means be secured to the vein.

Although the above described cuffs incorporate tabs for securing the cuff to tissue surrounding the vein, such tabs are not essential. Anchoring of the cuff may not always be required-for example, the location of the cuff may not permit movement of the cuff along the vein or the material of the cuff may possess sufficient friction with respect to the vein so as to prevent movement of the cuff along the vein.

The cuff may, of course, be of any convenient shape or configuration. As to its breadth (i.e. its dimension along the vein), the minimum requirement is that the cuff should cover substantially all of the cusps of the valve, preferably with some 1 to 1.5 mm excess at each end of the valve. The maximum breadth is limited by the general consideration that a single cuff should not span two venous valves.

The band is to be long enough to encircle the vein to which it is to be applied and to provide sufficient overlap to facilitate joining of the overlapping portions. As will be explained in more detail below, the overlapping arrangement of the band portions enables the circumference of the cuff to be reduced to the desired value at which competence is restored. That is to say, the cuff is applied in a dynamic way-the cuff circumference is initially larger than the diameter of the dilated vein and the circumference of the cuff is reduced until competency of the valve is detected.

The cuff may be manufactured from components as described above or formed as a one piece moulding.

EXAMPLE 1

A use of the cuff will now be described in relation to incompetence of the sapheno-femoral valve. The function of the sapheno-femoral valve is to decrease the pressure in the long saphenous system.

When the sapheno-femoral valve becomes incompetent, the vein distal to this point is exposed to abnormally high pressure which in turn causes dilatation of the vein below the sapheno-femoral valve and incompetence of the corresponding valve. This sequence continues until the thin-walled tributaries of the internal saphenous vein are also exposed to pressures that cause them to dilate, elongate and become tortuous-that is to say, they become varicose.

The above described sequential process commences because of the incompetence of the valve at the sapheno-femoral junction. Thus, if the functional defect of the valve is corrected by surgery, the patient will be substantially free from risk of further varicose veins.

The function of the cuff is to decrease the size of the sapheno-femoral vein at the valve site which pathplogically dilates and, as described above, the consequent incompetence of the valve causes varicose veins. The cuff is tightened around the vein at the valve site until the valve is assessed, during the operation, as being competent.

The standard surgical approach to the sapheno-femoral junction is used and the tributaries of the saphenous system are tied off before placing the cuff in position.

The sapheno-femoral valve band is so dimensioned as to encircle the sapheno-femoral vein at the valve site with the ends of the band overlapping so that they can be secured together in any convenient way. The sapheno-femoral valve can usually be seen through the vein wall and thus the cuff can be correctly located by inspection.

An integral securing tab may be provided in the mid portion of the strap that is preferably larger than the diameter of the vein at the valve. The securing tab may conveniently be of semi-circular shape and may be sutured to the cribriform fascia above the sapheno-femoral valve using fine non-absorbable sutures.

The use of the valve repairing cuff enables the main saphenous system to be left intact so that it may be used for coronary artery by-pass grafting, femoro-popliteal by-pass grafting and any of the other different types of by-pass grafting used in standard vascular surgery.

The varicose veins that actually appear in the legs are tributaries of the main long saphenous system and are dilated and become tortuous because the walls of these veins are exceedingly thin. On the other hand, the main long saphenous system itself has thick walls three to four times as thick as its tributaries and indeed has more muscle in its walls than any other vein in the body. Thus, this vein may be relatively normal whilst its tributaries become dilated. The insertion of the venous cuff at the sapheno-femoral junction preserves the long saphenous system and a standard removal of varicose tributaries can be performed at the same procedure.

EXAMPLE 2

It has been noted while using the venous cuff of the invention that the restoration of competence to a valve occurred rapidly at a critical circumference. A small increase in circumference resulted in a large increase in incompetence. Two studies examined this phenomenon, one in vivo and one in vitro.

The first study was performed on the left internal jugular vein of a sheep. A side to side arteriovenous anastamosis was performed proximal to a minimally incompetent valve. The vein was re-explored 2 weeks later and the pressure gradient was measured across the valve. The proximal pressure was a mean of 90 mmHg. The distal pressure was measured across the valve at different circumferences of the venous cuff. The initial circumference was 4 cm. This is a reflection of the degree of competence of the valve. The results were as follows:

TABLE 1

| Venous Cuff Circumference (cm) | Distal Pressure (mmHg) |
| --- | --- |
| 4.0 | 55 |
| 3.6 | 36 |
| 3.4 | 30 |
| 3.3 | 24 |
| 3.0 | 25 |
| 2.8 | 22 |
| 2.6 | 21 |
| 2.5 | 24 |

The venous pressure when the vein occluded was 23 mmHg which is the minimum pressure that the distal vein can achieve with a fully competent valve or with a circumference of 0 cm.

Figure 11:
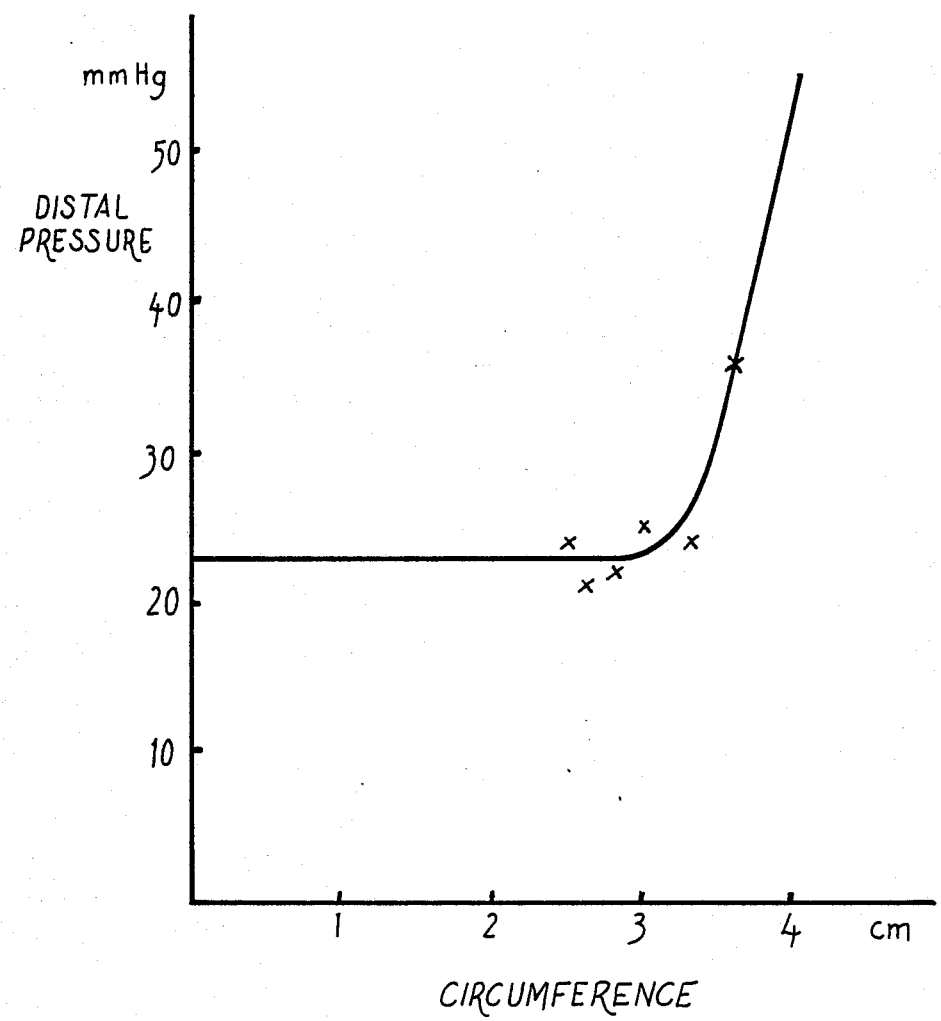
FIG. 11 is a graph of distal blood pressure against circumference of a vein at a valve site, and, FIG. 12 is a graph of retrograde resistance against vein circumference at a valve site.

FIG. 11 is a graph of the results in Table 1. It can be seen that only minimal improvement in competence can be made by reducing circumference below 3.3 cm. That is, a 17.5% reduction in circumference produced a near maximal effect on competence. Any further reduction in circumference is unnecessary and increases the risk of obstruction. The use of a special applicator allows a fine adjustment in circumference to be made and for competence to be continuously tested with successive small decreases in circumference.

EXAMPLE 3

The second study was on the right internal jugular vein of the same sheep. An in vitro set-up was used for this study. Hartmann's solution (Ringer's lactate) was perfused retrogradely from a standard intravenous infusion set at a height of approximately 1 meter. The distal vein was also connected to plastic tubing which was raised to run into a reservoir so that the distal pressure was a constant 5 mmHg. Pressures were measured 1 cm above and below the valve using the same equipment and methods as in the previous studies except that 19 G needles rather than cannulae were used.

The flow was measured using a measuring flask to measure outflow from the distal vein over 30 seconds. The results were as follows:

TABLE II

| Venous Cuff Circumference (cm) | Flow (ml/min) | Pressure Gradient (mmHg) | Retrograde Resistance |
| --- | --- | --- | --- |
| 3.6 | 146 | 2 | 0.01 |
| 3.0 | 81 | 5 | 0.06 |
| 2.6 | 5 | 80 | 16.0 |
| 2.5 | 3 | 90 | 30.0 |

Figure 12:
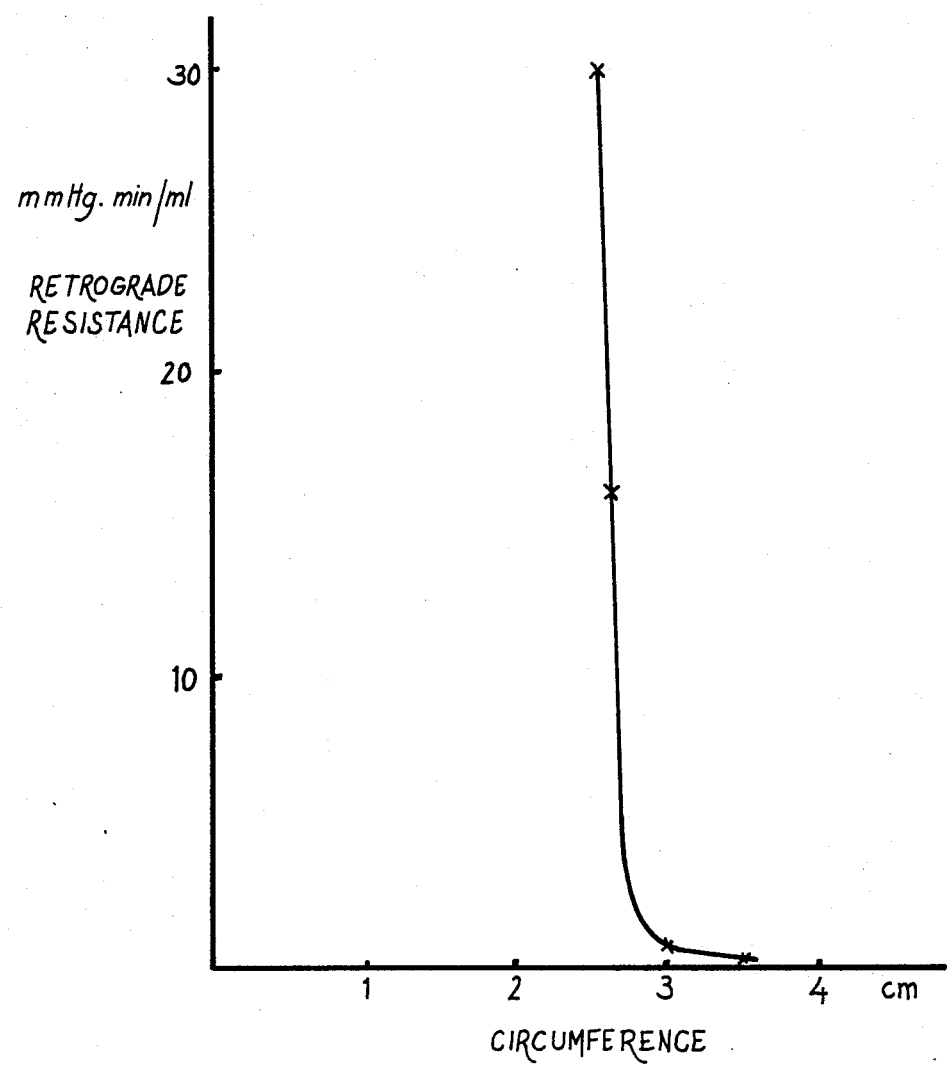

There was no increase in competence with further decreases in circumference unless the vein was occluded. The results shown in Table II are graphed in FIG. 12. Although insufficient points are plotted to be confident as to the exact best fitting curve, it is apparent that a large change in retrograde resistance is produced within a small range of change in circumference.

These studies on the biomechanics of the valve confirm the critical nature of circumference on competence. A narrow optimal range is apparent in these studies and can be observed by the surgeon while applying the venous cuff. If the vein is narrowed beyond this point, then a relative obstruction may be produced for no gain in competence. The choosing of the optimal circumference is aided by the use of an applicator which enables small increments in decreasing the circumference of the band and allows the surgeon to test competence by the "milking" technique. An optimal circumference can thus be found without narrowing the vein unnecessarily.

EXAMPLE 4

A venous cuff according to the invention has been used to restore competence to incompetent valves in ten internal jugular veins of sheep. All ten valves required a reduction in circumference of the dilated vein to produce a satisfactory degree of competence as is shown in the following table:

TABLE III

| SHEEP NO | JUGULAR VEIN | CIRCUMFERENCE IN CMS. | | PERCENTAGE DECREASE IN | |
|---|---|---|---|---|---|
| | | INITIAL | WITH CUFF | CIRC. | AREA |
| 86 | LEFT | 2.9 | 1.9 | 34 | 57 |
| | RIGHT | 2.5 | 2.1 | 16 | 29 |
| 87 | RIGHT | 3.5 | 2.2 | 37 | 60 |
| 88 | LEFT | 4.0 | 2.8 | 30 | 51 |
| | RIGHT | 3.9 | 2.8 | 28 | 48 |
| 89 | LEFT | 2.6 | 2.2 | 15 | 28 |
| | RIGHT | 2.7 | 2.0 | 26 | 25 |
| 90 | RIGHT | 1.9 | 1.5 | 21 | 38 |
| 91 | LEFT | 2.0 | 1.7 | 15 | 28 |
| | RIGHT | 2.4 | 2.0 | 17 | 31 |

The average reduction of circumference was 24% with a range of 15% to 34%. This is a moderate degree of narrowing but it must be placed in the context that veins are normally in a partially collapsed state when compressed by surrounding tissue. One vein was made incompetent by creating an arterio-venous fistula which caused dilatation of the valve ring. The reduction in circumference necessary to restore competence was 52%.

The animal model of venous valve incompetence is a useful one because, (i) The venous valves in the internal jugular vein in sheep appear macroscopically identical to the venous valves in humans. The histology of the vein wall is also similar.

(ii) The cause of the incompetence is the same as that which applies in over 90% of cases of varicose veins in at least 50% of cases of deep venous disease in humans, that is, hydrostatic pressure overcoming the strength of the vein.

(iii) An arteriovenous fistula has been found to mimic venous insufficiency in dogs, and has been used with proximal venous occlusion in dogs and rats. The arterio-venous fistula alone is sufficient to produce swelling of the limb in dogs and lymph changes which are similar to the disease of humans. It is also well known that an arteriovenous fistula can produce varicosities in humans and ulceration even of the upper limb.

(iv) The response of the vein wall histologically to a fistula has similarities to changes observed in saphenous veins in humans when used as an arterial graft particularly in the intimal proliferation, vein wall fibrosis and variable damage to the internal elastic lamina. The changes are, however, less severe.

(v) Destructive changes on the valve and vein wall are hastened both by the continuous application of a very high pressure to the valve and also by the pulsatile nature of the pressure which is thought to have an adverse affect on collagen.

In two sheep, incompetence of the valves developed quickly (within 5 days). This is despite the fact that these valves managed to remain competent for years (depending upon the age of the sheep) of normal function. The pressures on these valves normally would increase on grazing, when the head is lowered. The valves would be subjected to the hydrostatic pressure from the right atrium to the valve. The valves would also be subjected to pressures associated with coughing and Valsalva type maneuvers.

The implantation of the venous cuff protected the distal vein from the high pressure of the arteriovenous fistula. This was demonstrated convincingly by the measured pressure gradient and circumferences before and after implantation. In one sheep, this protective effect was still present nearly 9 weeks later at harvesting of the vein. From the results in this sheep it could reasonably be expected that this protective effect would last many years in the normal situation. This can be seen from the fact that the fistula had a destructive effect in five days greater than the life of the animal to that stage. Despite 9 weeks of this stress, the valve functioned well with the venous cuff implanted.

The venous cuff is very effective in preventing venous valve incompetence even in the presence of abnormally high pressures. These pressures created incompetence in the controls within two weeks yet this did not happen with the venous cuff in situ at a mean of 20 weeks. The importance of prevention of movement of the venous cuff along the vein led to the addition of tags or ears to the venous cuff to facilitate attachment to the surrounding fascia.

There was minimal damage to the vein wall and no complication attributable to the venous cuff itself. Comparison of light microscopy control and implant results showed that negligible effects on the vein wall are attributable to the venous cuff.

The silicone rubber sheet venous cuffs produced a similar reaction in all cases of implants. The macroscopic reaction to silicone rubber sheet around the adventitia of the vein was a smooth fine fibrous opaque white reaction. The silicone rubber sheet lifted easily away from the vein. There was no incorporation of the silicone rubber sheet into the vein wall and there was a small amount of clear serous fluid between the wall of the vein and the silicone rubber sheet.

The macroscopic appearance was that of serous membrane. When the vessel lumen was opened underneath the silicone rubber sheet cuff, there was minimal thickening of the wall.

The intimal lining itself appeared macroscopically identical to the surrounding intima. There was no evidence of any thrombotic process, no ulceration, no fibrotic obstruction, no haemorrhage into the wall and no thickening of the vein wall. One sheep had a decrease in the diameter of the wall distal to the implant. This appeared to be related to a subcutaneous suture distally which was compressing the vein. This was not associated with the silicone cuffs themselves.

Based on microscopic observation, light microscopy, scanning electron microscopy and pressure measurements, the following conclusions can be drawn from the above animal studies.

The venous cuff is made from a material with favourable biocompatibility characteristics in terms of interactions with veins. There was minimal or no difference in histology of implant specimens and control specimens on the vein wall. Out of 50 implants in animals, there have only been three complications with two implants. There were two infections and one thrombosis. This thrombosis was probably caused by the pressure measurement technique. The two infections would be expected with any operation. The silicone cuff has not caused complications beyond those expected with any similar operation with no implant. Thus no complication can be directly attributed to the cuff.

The venous cuff is highly successful at restoring competence to incompetent venous valves which are not destroyed by thrombophlebitis. Competence was markedly improved in all 20 of 20 valves in animal models. The improvement is maintained at a mean implant time of 12 weeks. This is also supported by six implants which prevented incompetence despite very high retrograde pressure gradient for a mean implant time of 20 weeks and a maximum of 28 weeks implant time.

The animal models are confirmed by the human work. The only complication out of 16 implants was one infection which had no long-term morbidity after removal of the cuff. There were two prophylatic implants. The implant of the cuff produced competence in twelve out of the remaining thirteen valves. The other valve was affected by thrombophlebitis, which is now regarded as a relative contra-indication to the procedure. Of these thirteen valves, ten were for varicose veins and all patients had resolution of symptons. The mean implant time was 25 weeks. The longest implant was 15 months. This long-term implant has had no recurrence of an ulcer which was present five months continuous preoperatively. The remaining three implants were on a patient with deep venous disease. He had healing of his ulcers and has minimal symptoms three months postoperatively.

The venous cuff of the invention is a safe, reliable device for producing long-term competence in incompetent venous valves. This produces a corresponding resolution of symptoms in people with varicose veins and chronic deep venous insufficiency.

The venous cuff may be placed into position and tightened around the vein by the use of an applicator such as that described in our Australian patent application PI 0271 filed on 10 Feb. 1987. Such an applicator has an upstanding tab which receives the loop of the cuff. The cuff is then passed around the vein and the free end of the cuff connected to a cuff adjustor mounted on the applicator body with a ratchet mechanism which allows the adjustor to be moved relative to the applicator and to be held in any selected position. A stapling gun incorporated within the applicator is used to secure the overlapping end of the cuff to the loop 13.

As will be apparent from the above description, the applicator allows a single surgeon to apply the cuff to a vein. With one hand, the surgeon using the applicator can adjust the cuff to the desired diameter and then test the valve for competence. After final adjustment of the diameter, the surgeon then staples the overlapping portions of the cuff together. If need be, the free end of the band is trimmed and the cuff removed from the applicator.

Various modifications may be made in details of the cuff and the method of restoring venous valve competency without departing from the scope and ambit of the invention.

What is claimed:

1. A cuff for restoring competence to an incompetent venous valve, said cuff comprising a band of biocompatible implantable material that is not stretchable at blood flow pressures, the band being of sufficient length to encompass the vein at the site of the venous valve with portions of the band overlapping, the overlapping portions being joinable together to form a cuff of desired circumference small enough to restore competence yet not too tight to decrease blood flow; and said band being notched to accommodate application at a venous junction.

2. A cuff for restoring competence to an incompetent venous valve, said cuff comprising a band of biocompatible implantable material that is not stretchable at blood flow pressures, the band being of sufficient length to encompass the vein at the sight of the venous vale, with portions of the band overlapping, means for securing the overlapping portions together to form a cuff of desired circumference small enough to restore competence yet not too tight to decrease blood flow; and said band being notched to accommodate application at a venous junction.

3. A cuff according to claim 1 or claim 2 and further including means for securing the cuff to the surrounding tissue.

4. A cuff according to claim 3 wherein the securing means comprises a pair of tabs secured one at each end of a transverse portion that extends outwardly from either side of the band.

5. A cuff according to claim 1 or 2 wherein the securing means includes tabs secured to or integral with each transverse portion.

6. A cuff according to claim 1 or claim 2 and further including loop means at or adjacent one end of the band, said loop being spaced from the band so as to receive the other end of the band.

7. A cuff according to claim 6 wherein said other end of the band receiver within the loop is secured to the loop to form the cuff of desired circumference.

8. A cuff according to claim 1 or claim 2 and further including means at or adjacent one end of the band for attaching the band to an applicator.

9. A cuff according to claim 1 or claim 2 wherein the band has at one end connector means comprising an elongated strap of implantable material disposed transversely to the band, said strap having inwardly directed slits that divide the connector means into a band attachment portion and an outer deformable portion.

10. A cuff according to claim 9 wherein the deformable portion extends outwardly from each side of the band and constitutes means for securing the cuff to the surrounding tissue.

11. A cuff according to claim 10 wherein the securing means includes a tab secured to or integral with each transverse portion.

12. A cuff according to claim 10 wherein the band attachment portion includes a loop disposed above the band.

13. A cuff according to claim 1 wherein the implantable material comprises a composite including a reinforcing fabric.

14. A cuff according to claim 1 wherein the implantable material is cured silicone rubber sheeting.

15. A cuff according to claim 14 wherein the cured silicone rubber sheeting is reinforced with a woven polyester.

16. A method of restoring competency to incompetent venous valves comprising the steps of:
   (i) placing a cuff of biocompatible material around the vein at the site of the valve,
   (ii) reducing the circumference of the cuff (and hence the diameter of the vein at the valve site) until competency of the valve in the vein is restored, and,
   (iii) fixing the diameter of the cuff at the point where the diameter of the vein is reduced to restore competency of the valve without impairing blood flow.

17. A method according to claim 16 and further including the step of securing the cuff to neighbouring tissue after its circumference has been fixed.

18. A method according to claim 16 or claim 17 wherein the diameter of the cuff is reduced in a stepwise fashion with the competency of the valve being tested between each stepped reduction in the circumference of the cuff.

* * * * *